United States Patent [19]

Wallock et al.

[11] Patent Number: 5,308,406

[45] Date of Patent: May 3, 1994

[54] CLEANING OF HEALTH CARE INSTRUMENTS

[76] Inventors: Joan Wallock, 836 Bonnie Brae La.; James M. Leu, 159 Thornhurst, both of Bolingbrook, Ill. 60440

[21] Appl. No.: 990,015

[22] Filed: Dec. 14, 1992

[51] Int. Cl.⁵ .................... B08B 1/00; B08B 7/00
[52] U.S. Cl. .................... 134/42; 15/104.92; 15/104.5; 15/21.2
[58] Field of Search ............ 134/42; 15/104.92, 104.5, 15/21.2

[56] References Cited

U.S. PATENT DOCUMENTS

| | | | |
|---|---|---|---|
| 4,439,884 | 4/1984 | Giorni | 15/104.92 |
| 5,093,079 | 3/1992 | Bakaitis et al. | 15/104.92 |

Primary Examiner—R. Bruce Breneman
Assistant Examiner—Zeinab El-Arini
Attorney, Agent, or Firm—Hill, Steadman & Simpson

[57] ABSTRACT

A method for cleaning soiled health care instruments involving subjecting the soiled surfaces of the instruments to a surrounding array of generally inwardly directed cleansing bristles. The bristles are carried by a tubularly bent flexible panel within a tubular container. The container has opposite ends one of which is closed and the oppose of which permits cleansing entry of instruments into the container. Said opposite end may have a self-sealing door entrance for projections therethrough of the instruments to be cleaned. Protection is provided against injury from exposed sharp edges of the instruments being cleaned. Liquid cleaning simultaneously with the bristle cleansing is provided for.

20 Claims, 2 Drawing Sheets

CLEANING OF HEALTH CARE INSTRUMENTS

BACKGROUND OF THE INVENTION

This invention relates in general to the cleaning of health care instruments prior to sterilization, and is especially useful in cleaning sharp ended cutting and probing medical and dental instruments which are employed in the course of health care delivery services.

During routine procedures performed on patients, reusable health care instruments may accumulate organic and inorganic debris that must be removed prior to sterilization as is necessary before such instruments are reusable for their intended purpose.

Common disinfection and sterilization procedures are often not capable of removing solids that may have accumulated on the instruments during use.

For example, blood has long been recognized as a potential source of pathogenic microorganisms that may present a risk to individuals who are exposed during the performance of their duties. In 1983 the CDC published guidelines for controlling infections in hospitals. One section, entitled "Blood and Body Fluid Precautions," recommended that certain precautions be taken in handling the blood and body fluids of patients who were known infected, or were suspected of being infected, with bloodborne pathogens. Special precautions were recommended to be followed with such patients.

Most sterilization procedures employ soaking and extreme heating but not friction to dislodge and remove accumulated solids.

The most universally accepted and time-tested procedure to remove solids has customarily been to use a hand held bristle brush such as a nylon bristle nail brush or a tooth brush. The technician holds an instrument in one hand and strikes and/or brushes the instrument with a bristled brush wielded by the other hand.

More recently, ultrasonic cleaning has also been used compared to handheld brushing. This procedure is viewed at least as an additional method of cleaning and some authorities contend it is superior to hand scrubbing. Ultrasonic cleaning does, however, require machinery, expensive maintenance and considerable expenditure of time in its practice. Ultrasonic cleaning will not, in all cases, remove dried and hardened matter adhering to an instrument. A preponderance of authorities agree that ultrasonic cleaning is most effective when used in conjunction with hand brushing.

Hand-held, reusable instruments utilized in health care delivery, and especially in dentistry, often have a working end at each end of the instrument that can be pointed and/or cutting blade sharp. The design of these instruments permits probing and cutting of hard and soft tissue in the mouth and shaping and carving of dental restorative materials. The functional ends of these instruments present serious risk of cuts and puncture to the technician cleaning them and especially while the technician is attempting to remove accumulated solids from the instruments by use of a hand-held bristle brush. Debris accumulated on the contaminated instruments contains microorganisms that can infect the technician. These microorganisms may include hepatitis, HIV, and a myriad of other infectious diseases that pose a serious health risk to the technician handling a soiled instrument.

There does not appear to be any adequate scrubbing device presently available to health care providers that permits hand-held reusable instruments to be cleaned manually and without risk of infection to the technician from a contaminated instrument in the event of a cut or puncture wound from that instrument.

SUMMARY OF THE PRESENT INVENTION

An important object of the present invention is to provide a new and improved method of and means for cleaning of health care instruments which may have adhering use-acquired debris.

Another object of the present invention is to reduce the liability of contaminating injury from soiled health care instruments, during cleaning thereof.

A further object of the present invention is to provide a method of and means for cleaning of health care instruments, which will reduce decontamination time, will lower the level of pathogenic aerolization, and Will avoid contamination of environmental cleaning area.

Yet another object of this invention is to provide a new and more efficient manual method of and means for cleaning soiled medical or dental instruments, generally referred to herein as health care instruments.

According to the principles of the present invention there is provided a new and improved method of and means for cleaning soiled health care instruments, involving subjecting the instruments to the cleansing action of an array of inwardly directed cleansing bristles.

The invention also provides a new and improved environmentally safe method of and means for cleaning health care instruments.

BRIEF DESCRIPTION OF THE DRAWINGS

Other objects, features, and advantages of the present invention will be readily apparent from the following description of certain representative embodiments thereof, taken in conjunction with the accompanying drawings although variations and modifications may be effected without departing from the spirit and scope of the novel concepts embodied in the disclosure, and in which.

DETAILED DESCRIPTION

Figure 3:
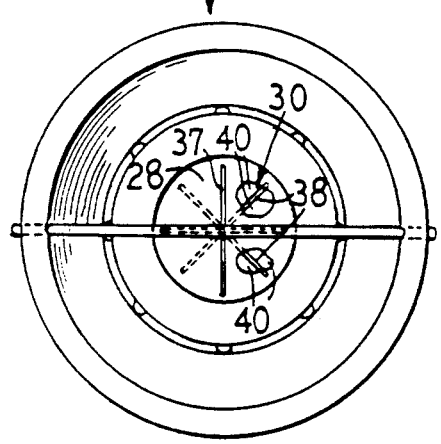
FIG. 3 is a top plan view of the device of FIGS. 1 and 2.
Figure 4:
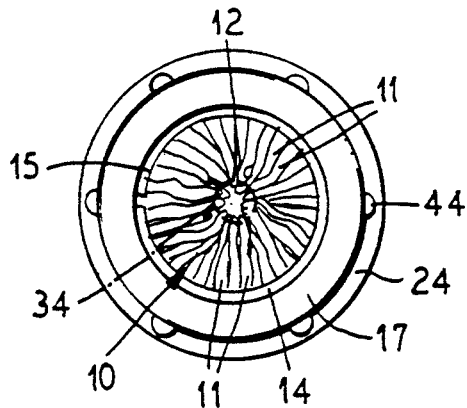
FIG. 4 is a transverse sectional detail view taken substantially along the line IV-IV in FIG. 2.

In best mode form, the present invention provides for cleaning of soiled health care instruments by subjecting them within a device 9 to internal cleaning brush means 10 (FIGS. 2, 3 and 7) comprising an array of generally inwardly directed, and in this instance convergently related, closely packed, flexibly resilient bristles 11 having their inner ends 12 close to a longitudinal axis 13 of the brush means. In a convenient form, the brush means 10 comprises a resiliently flexible backing panel pad 14 which may be fabricated from a plastic material which is non-absorptive and non-porous, with resistance to solvents and disinfectants, and highly resistant to fracture, corrosion and puncture. The bristles 11 extend permanently from one surface of the base pad 14 and may be fabricated from the same or a different material but preferably fused, if appropriate, or otherwise permanently attached to the base pad 14. As fabricated the pad 14 is desirably a spread out substantially flat resilient panel, as shown in FIG. 8, and which is readily adapted to be curled into tubular form as best seen in FIG. 4, wherein end edges 15 are brought into at least close proximity in the tubular form. A readily available material for this purpose is Astroturf® a proprietary product of Astroturf Industries, Inc., St. Louis, Mo., U.S.A.

A body component of the device 9 comprises a container 17 for the brush 10 in the form of a tubular body casing or housing which is preferably constructed from a rigid or semi-rigid impervious material, such as plastic, ceramic, metal, or the like, suitable for the intended use. An inner tubular wall 18 of the housing 17 is of a diameter and length to receive the base wall of the tubularly curled brush pad panel 14 in a snug uncurling expanding spring frictional gripping relation in an upper portion of the wall 18 so as to resist longitudinal displacement within the container. It will be observed in FIG. 2 that the brush 10 may be of substantial length but somewhat shorter than the tubular housing casing 17 so that there may be a sump space 19 in the lower part of the housing. If desired, of course, the brush 10 may be permanently bonded to the wall 18.

Desirably, the construction and arrangement of the brush 10 and housing 17 assembly are such that they can be separated for cleaning when desired and easily rejoined or replaced. For this purpose, the lower end of the housing 17 is open and is closable in fluid tight relation by means of a cap 20 secured in place replaceably as by means of threads 21. Intermediate its ends the tubular housing 17 may be provided on its outer wall with circumferentially spaced longitudinally extending finger grip ribs 22.

Figure 1:
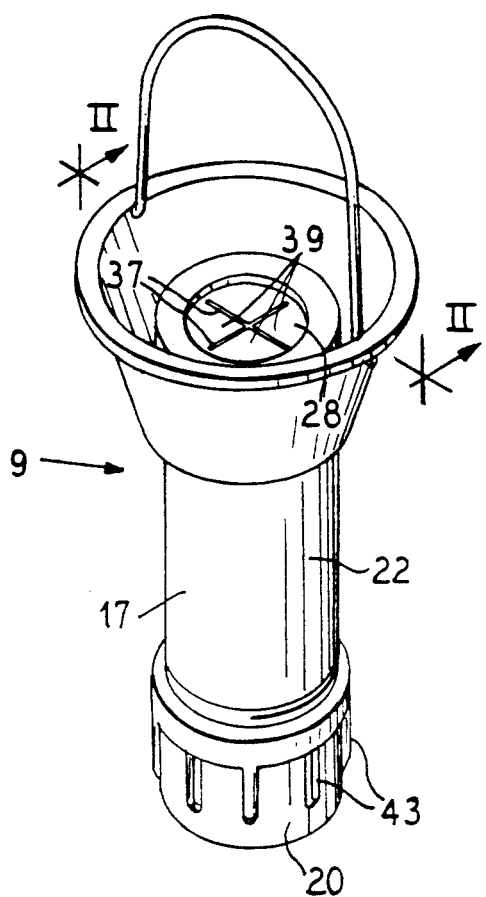
FIG. 1 is a perspective view of a new and improved device for practice of the present invention.
Figure 2:
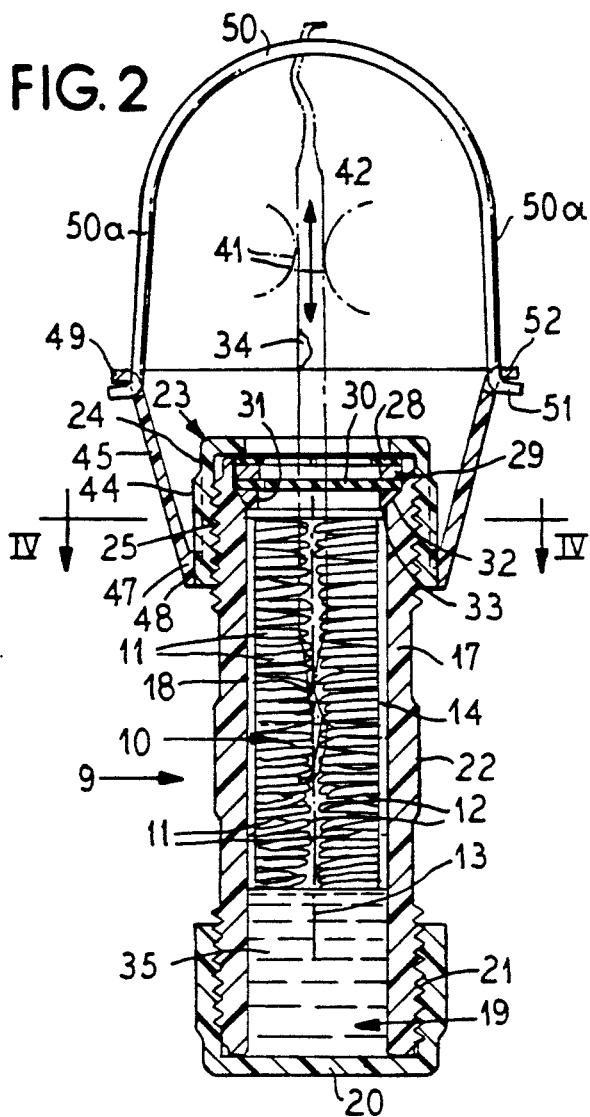
FIG. 2 is a vertical sectional detail view taken substantially along the line II-II of FIG. 1.

At its upper end, the tubular casing 17 is also constructed as an open ended, tube, but closed in service by means of a cap assembly 23 which is removably attached. In a desirable arrangement, the cap assembly 23 comprises a ferrule 24 which is secured by means of complementary threads 25 to the upper end portion of the tubular housing 17. A radially inwardly project retainer flange 27 at the upper end of the ferrule 24 is adapted to overlie the upper end of the housing 17 and serves as a holddown or clamp for associated element means of the assembly. As shown in FIGS. 1-3, the means clamped in place by the flange 27 comprises a substantially leak-proof assembly of elements including a resiliently flexible disk 28 stacked at its margin on an annular sealing ring 29 which in turn is stacked on the margin of an underlying second resiliently flexible sealing disk 30 marginally engaged and stacked on an underlying generally triangularly cross-sectioned annular sealing ring 31 which has an annular oblique, hypotenuse sealing surface 32 engaging a complementary oblique annular sealing surface 33 provided by the cooperating upper end portion of the housing 17.

The flexibly resilient disks 28 and 30 serve the multiple functions of leak-resistant barrier, splash and aerolization guard and self-sealing entry or doorway for a health care instrument 34 inserted for cleansing by means of the brush 10 and flushing by means of a flushing liquid 35 contained in the sump 19. Entry of the end portion of the instrument 34 to be cleaned is permitted by the provision in the outer disk 28 of crossing slits 37, and the provision of similar crossing slits 38 in the inner disk 30. Thereby, the instrument 34 is adapted to be inserted endwise through the disks 28 and 30 by resiliently flexible yielding of the central areas of the disks separated into cooperating generally triangular flaps 39 and 40, respectively, which yield inwardly when the instrument is inserted and resume their sealing coaction when the instrument is withdrawn. Improved sealing cooperation of the cross slit disks is obtained by having the slits 37 of the upper disk 28 angularly offset relative to the slits 38 of the lower disk 30, as best seen in FIG. 3.

It will thus be apparent that elongated health care instruments 34 can be easily, efficiently cleaned by simple digital 41 agitation including longitudinal manipulation into the device through the, in effect, self-sealing doorway provided through the disks 28 and 30, and longitudinally scrubbingly working up and down, as indicated by the directional arrow 42 in FIG. 2. At least half of the lower portion of the instrument 34 may be subjected to the abrasive, debris dislodging action of the bristles 11 and more particularly the tips 12 of the bristles. In addition to the up and down agitating motion applied to the instrument 34, there may be an accompanying rotating motion so that all parts of the instrument surfaces being cleaned will be assuredly reached by the cleansing bristles. The liquid 19 may be any preferred flushing, solvent, detergent, antiseptic material suitable for the purpose. The cleaning person may repeatedly insert the instrument 34 for cleaning, and remove it for inspection to see whether cleaning has progressed satisfactorily, as often as necessary. During the cleaning maneuver the sealing disk flaps 39 and 40 will avoid splashing of the cleansing liquid 19, and when the instrument has been withdrawn from the cleaning environment of the device the sealing disk and gasket assembly avoids leakage or spillage of the cleaning liquid from the device. Cleaning of the components of the device is easily effected by removal of the lower end cap 20 and the upper retaining ferrule 24. Digital maneuvering of the threadly attached parts is facilitated by the antiskid gripping ribs 22 on the housing tube 17, and similar antiskid gripping ribs 43 on the lower end cap 20 and gripping ribs 44 on the ferrule 24.

While in use, the cleaning device 9 is adapted to be held in one hand of the user while the instrument 34 is maneuvered by the other hand of the user. Should for any reason the end of the instrument 34 to be cleaned be improperly directed toward the top entry into the cleaning device, either initially or during possible escape in the course of reciprocating vigorous cleaning agitation of the instrument, the lower pointed end of the instrument is liable to puncture the unprotected hand holding the cleaning device. Therefore, means are provided herein to protect against such injury, comprising an upwardly flaring guard collar 45 having at its lower end an internal annular attachment lip or rib 47 complementary to a lower end, external frictionally engageable, circular supporting surface 48 on the ferrule 24.

Thereby, the safety collar 45 can be dismounted for cleaning, and readily replaced frictionally as needed.

From the collar 47, the guard 45 flares upwardly cup-like to a distance above the upper end of the ferrule 24 sufficient to protectively capture and divert inwardly the lower end of the instrument 34 should it possibly be misdirected relative to the entrance into the cleaning device. As shown, the safety collar 45 desirably extends above the ferrule 24 as high as one-half the length of the ferrule. To reinforce the upper end of the safety collar 45, it is provided with an annular radially outwardly extending reinforcing rim flange 49.

To guard against injury to the hand or fingers, represented schematically at 41, manipulating the instrument 34 during the cleaning operation by grasping the upper end portion of the instrument, where that end has a sharp working tip, means are provided in the form of an overhead member such as a wicket-like upstanding guard hoop 50. The hoop 50 has legs 50a provided at their lower ends with outwardly extending latch terminals 51 which are engageable in complementary sockets 52 formed at juncture of the reinforcing rim flange 49 with the body of the guard member 45. By having the guard hoop 50 of a resilient wire construction, the guard hoop can be readily mounted into the assembled relation with the guard member 45 and removed as desired, by squeezing the hoop legs 50a toward one another for clearing the sockets 52, and for automatic snap-in engagement of the terminals 51 into the sockets 52 when lined up with the sockets during assembly. In a practical arrangement, the guard hoop 50 may extend to on the order of two to three inches above the top of the guard member 45.

Figure 5:
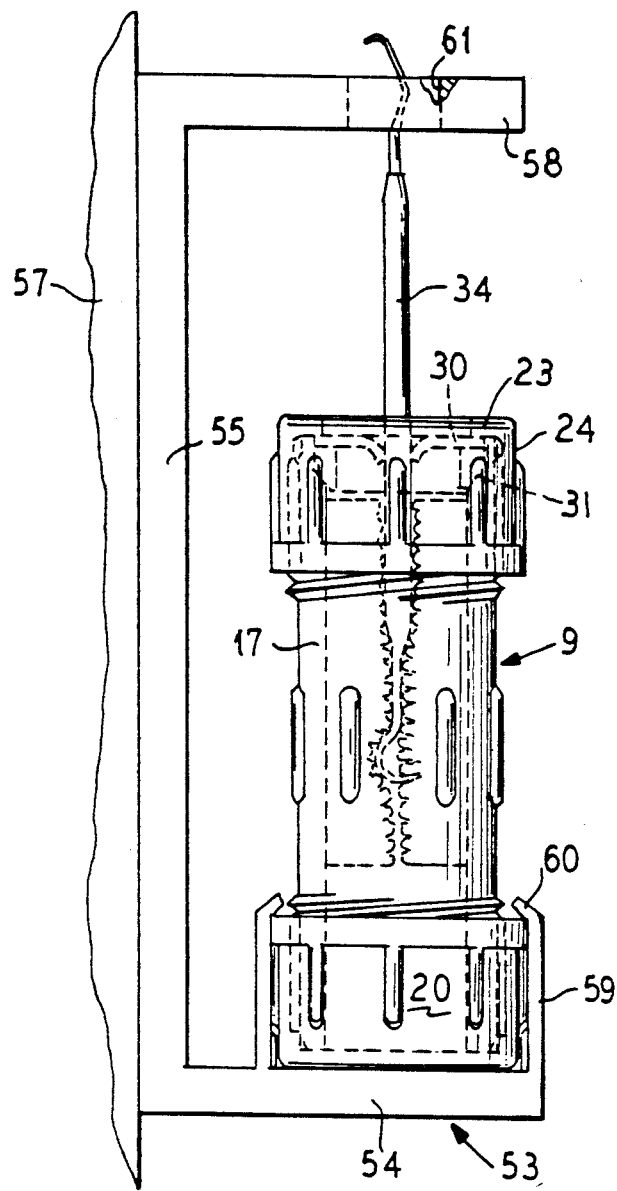
FIG. 5 is an elevational view of a slight modification of the cleaning device of the present invention showing the same mounted on a supporting bracket.
Figure 6:
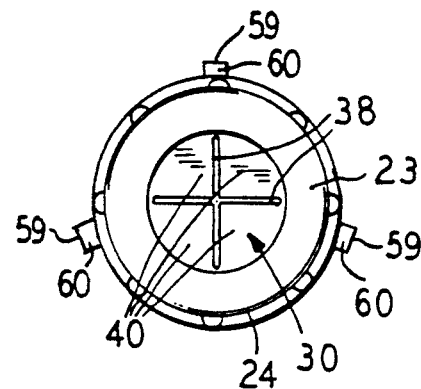
FIG. 6 is a top plan view of the cleaning device of FIG. 5.

If preferred, the device 9 may be mounted on a bracket 53 (FIG. 5). For this purpose the bracket 53 may have a platform 54 on which the device 9 is received, a mounting back 55 secured to a stand or wall 57, and an upper end safety guard means projection or flange 58 overlying the base panel 54 in suitably spaced relation. On the base panel 54 means for retaining the device 9 removably make comprise a set of resiliently flexible retaining fingers 59 constructed complementary to the lower closure cap 20 so that upper end inturned retaining lugs 60 on the fingers 59 can grip the upper edge of the cap 20 in a snap-in retaining engagement. Thereby, the device 9 can be easily snapped into position relative to the fingers 59 on the bracket 53 or removed by snapping the device from the fingers 59 as when it is desired to clean the device 9.

The overhanging guard flange 58 is located at a height sufficient to permit easy insertion of the health care instrument 34 into the instrument 9, cleaning agitation of the instrument, and removable thereof, while nevertheless providing a guard against injury of the instrument manipulating hand of the person agitating the instrument during cleaning. Desirably the upper end portion of the instrument 34 extends through a clearance hole 61 in the guard flange 58 during at least a portion of the cleaning maneuver agitation of the instrument.

The device 9 in FIG. 5 may be the same in all particulars as the device 9 in FIGS. 1 and 2, except that the guard collar 45 and the guard loop 50 supported thereby are omitted, because the device 9 in FIG. 5 is supported in a fixed position in use, and a less elaborate upper end sealing arrangement may be used. Therefore, only one of the top end self-sealing doorway disks such as the disk 30 stacked on the sealing ring 31 may be clamped in place by the clamping flange 23 of the ferrule 24, as a splash guard.

Figure 7:
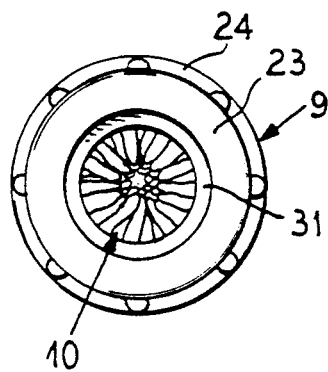
FIG. 7 is a top plan view similar to FIG. 6, but showing a modification.
Figure 8:
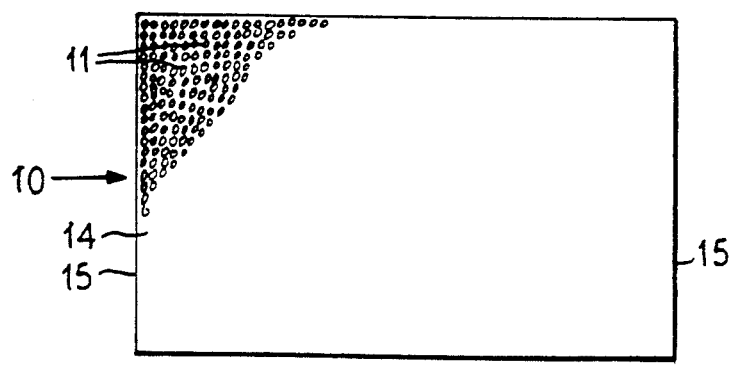
FIG. 8 is a plan view of a spread-out bristle mounting panel of the type that is adapted to be used the devices of FIG. 1, FIG. 5 and FIG. 7.

If it is preferred to use the device 9 without the self sealing upper end doorway disks 28 or 30, these disks may be omitted as shown in FIG. 7 and the clamping flange 23 of the ferrule 24 simply sealingly caused to clamp the sealing ring 31 of the device. This arrangement may require greater care against splashing of cleansing liquid carried by the sump within the device.

From the foregoing it will be apparent that the present invention provides for substantially better cleaning of health care instruments by subjecting them to greatly improved frictional cleaning action than ordinarily obtainable with a hand held brushing action. During the brushing, frictional cleaning, simultaneous liquid flushing can be practiced. There is greatly reduced level of pathogenic aerolization. Decontaminating time is substantially reduced. Excellent protection against incidental punctures from contaminated instruments is attained. Debris cleaned from the instruments is retained within a small clean up area, substantially free from environmental contamination.

Although other modifications and changes may be suggested by those skilled in the art, it is the intention of the inventors to embody within the patent warranted hereon all changes and modifications as reasonably and properly come within the scope of their contribution to the art.

We claim as our invention:

1. A new and improved method of cleaning elongate soiled health care instruments, comprising:
   providing a tubular container having opposite ends, one of which ends is closed and opposite end is open for projection therethrough into the container of instruments to be cleaned;
   providing a flexible panel having instrument-cleaning bristles on one face thereof;
   bending the panel into substantially tubular form and thereby directing said bristles generally convergently towards one another about an axis;
   inserting said tubularly bent panel into said container; instruments to be cleaned and relatively agitating said instruments and the bristles in contact with the instruments and thereby effecting cleansing of the instruments by the bristles.

2. A method according to claim 1, which comprises subjecting the instruments to cleaning liquid within the container simultaneously with the cleansing agitation.

3. A method according to claim 1, which comprises inserting soiled portions of the instruments seriatim into the container through a self-sealing door extending across said open end, and effecting said agitating manually.

4. A method according to claim 1, which comprises effecting said agitating in the presence of means at said open end guarding against injury from exposed sharp ends of the instruments.

5. A method according to claim 4, which comprises effecting said guarding by manipulating said instruments within the protective ambit of hoop means.

6. A method according to claim 4, which comprises effecting said guarding under an overhanging protective flange means.

7. A method according to claim 1, which comprises holding said container in one hand, while manipulating the instruments with the other hand.

8. A method according to claim 1, which comprises supporting said container on a supporting bracket, and as thus supported manipulating the instruments to be cleaned manually.

9. A new and improved method of cleaning elongate soiled health care instruments, such as dental instruments, comprising:
   providing a tubular container having opposite ends;
   closing one end of the container with a removable cap;
   providing within said container generally convergently related cleansing bristles;
   providing an opening into the opposite end of the container;
   inserting into said container, through said opposite end opening portions of instruments to be cleaned and engaging the thus inserted portions of the instruments with said cleansing bristles; and
   moving said instruments relative to said bristles and thereby cleansing said portions by action of the bristles on said portions.

10. A method according to claim 9, which comprises, providing at said opening a retaining ferrule, after cleansing of said portions of the instruments withdrawing the instruments from the container, removing, with the assistance of finger grip ribs thereon, at least one of said cap and ferrule from the container, removing said bristles from said container, and cleaning the container and said bristles.

11. A method according to claim 9 which comprises holding said container in one hand, grasping the instruments in the other hand and effecting said moving, and guarding said hands against injury from any sharp edges of the instruments.

12. A method according to claim 11, which comprises effecting said guarding at least in part by means of a guard loop over said opening.

13. A method according to claim 11, which comprises effecting said guarding at least in part by means of a generally cup-like guard member attached about said opening.

14. A method according to claim 9, which comprises providing at said opening a flexible self-closing door, and inserting said portions of the instruments through said door into said container and into cleansing engagement with said bristles.

15. A method according to claim 14, which comprises providing said door as a flexible disk having crossing slits, securing said disk to said container over said opening, inserting said instruments through said slits into the container, and by means of flaps between the slits avoiding escape from within the container of material placed in 16. A method according to claim 15, which comprises providing a second flexible disk, providing said second flexible disk with crossing slits, attaching said second disk to said container in adjacently parallel relation to said first mentioned disk, and inserting said instruments through the slits of both of said disks into cleansing engagement with said bristles in said container.

17. A method according to claim 14, which comprises providing a body of cleaning solution in said container, by means of said self-closing door preventing splash of said solution during cleansing movement of said instruments, avoiding aerolization, and resisting leakage from said container.

18. A new and improved method of cleaning health care instruments having sharp edges, comprising:
   hand manipulating said instruments with at least portions of the instruments to be cleaned extending into a container having cleansing bristles therein, and moving the instruments relative to the bristles;
   and by guard means associated with the container guarding the instrumentagitating hand against instrument sharp edge injury.

19. A method according to claim 18, which comprises effecting said guarding by means carried by said container.

20. A method according to claim 18, which comprises effecting said guarding by means overhanging said container, and supporting said container on a support below said overhanging guarding means.

* * * * *